United States Patent [19]

Parran, Jr.

[11] 4,323,551
[45] Apr. 6, 1982

[54] MOUTHWASH COMPOSITIONS

[75] Inventor: John J. Parran, Jr., Cincinnati, Ohio

[73] Assignee: The Procter & Gamble Company, Cincinnati, Ohio

[21] Appl. No.: 235,873

[22] Filed: Feb. 19, 1981

[51] Int. Cl.³ .......................... A61K 7/16; A61K 7/22
[52] U.S. Cl. .......................................... 424/54; 424/57
[58] Field of Search ...................................... 424/49–58

[56] References Cited

U.S. PATENT DOCUMENTS

| | | | |
|---|---|---|---|
| 2,041,473 | 5/1936 | Janota | 424/57 |
| 2,921,885 | 1/1960 | Bouchal | 424/54 |
| 3,137,632 | 6/1964 | Schiraldi | 424/57 |
| 3,355,392 | 11/1967 | Cantor et al. | |
| 3,462,525 | 8/1969 | Levinsky | 424/54 |
| 3,507,796 | 4/1970 | Voss | |
| 3,703,583 | 11/1972 | Martin | 424/54 |
| 3,927,201 | 12/1975 | Baines et al. | |
| 3,956,479 | 5/1976 | Bauman | |
| 3,957,964 | 5/1976 | Grimm | |
| 3,959,458 | 5/1976 | Agricola et al. | |
| 3,976,765 | 8/1976 | Nachtigal | 424/54 |
| 4,003,971 | 1/1977 | Mannara | |
| 4,042,679 | 8/1977 | Gaffar | |
| 4,130,636 | 12/1978 | Tomlinson | 424/57 |
| 4,130,637 | 12/1978 | Bauman | 424/54 |
| 4,150,151 | 4/1979 | Pader et al. | 424/56 |
| 4,183,916 | 1/1980 | Rodon | 424/54 |
| 4,213,961 | 7/1980 | Curtis et al. | 424/54 |
| 4,224,309 | 9/1980 | Gaffar et al. | |
| 4,264,580 | 4/1981 | Barberio | 424/57 |

*Primary Examiner*—Shep K. Rose
*Attorney, Agent, or Firm*—Douglas C. Mohl; John V. Gorman; Richard C. Witte

[57] ABSTRACT

Mouthwash compositions exhibiting plaque control while also having reduced staining tendencies comprising a quaternary ammonium compound, a pyrophosphate salt and having a pH within the range of 7.0 to 9.5, said compositions being adjusted to that range with an acid.

10 Claims, No Drawings

4,323,551

MOUTHWASH COMPOSITIONS

TECHNICAL FIELD

The present invention relates to novel mouthwash compositions which exhibit plaque control as well as reduced staining. Furthermore, the compositions have improved turbidity.

Bacteria which are present in the oral cavity lead to plaque formation. For this reason, it has been known to include cationic antibacterial materials which are effective against the bacteria in oral compositions. However, these cationic antibacterial materials, when used in amounts which are effective, have frequently exhibited undesirable discoloration of the teeth. For this reason, many attempts have been made to develop antiplaque compositions with reduced staining.

BACKGROUND ART

To alleviate the staining caused by cationic bacterial agents, a variety of materials have been included in compositions containing the agents. These materials include a wide variety of chemical types with phosphorus containing compounds frequently used.

Included among the phosphorus containing agents used in oral compositions are disodium ethane 1-hydroxy 1-diphosphonic acid as shown in U.S. Pat. No. 3,959,458, May 25, 1976 to Agricola et al. Other phosphorus containing agents are polymeric polyphosphonic compounds disclosed in U.S. Pat. No. 4,042,679, Aug. 16, 1977 to Gaffar and its related patents. A third patent disclosing a particular phosphorus containing compound, namely, 2-phosphonobutane-1,2,4 tricarboxylic acid, is U.S. Pat. No. 4,224,309, Sept. 23, 1980 to Gaffar et al.

In addition to the above references, the prior art discloses compositions, although not necessarily mouthwash compositions, containing quaternary ammonium compounds and pyrophosphate salts. Included among such references are U.S. Pat. No. 3,507,796, Apr. 21, 1970 to Voss and U.S. Pat. No. 3,355,392, Nov. 28, 1967 to Cantor et al. Additional references disclosing pyrophosphate salts in a variety of oral products include U.S. Pat. No. 3,956,479, May 11, 1976 to Baumann; U.S. Pat. No. 3,957,964, May 18, 1976 to Grimm; and U.S. Pat. No. 4,003,971, Jan. 18, 1977 to Mannara.

While these references disclose the use of pyrophosphate salts in combination with cationic antibacterial agents, they do not suggest the invention claimed herein.

It is an object of the present invention to obtain an effective antiplaque mouthwash which also has reduced staining characteristics.

It is a further object of the present invention to provide an effective antiplaque mouthwash having improved turbidity.

These and other objectives of the present invention will become obvious from the detailed disclosure which follows.

DISCLOSURE OF THE INVENTION

The present invention relates to mouthwash compositions comprising from about 0.02 to 0.20% of a quaternary ammonium compound, an amount of a tetra-alkali metal pyrophosphate salt sufficient to provide from about 0.5% to 5% of the $P_2O_7^{-4}$ species, an amount sufficient of an acid to adjust the pH of the composition to within the range of 7.0 to 9.5 and a carrier liquid.

DETAILED DESCRIPTION OF THE INVENTION

It has been discovered that compositions comprising the above generally described components possess antiplaque activity while also exhibiting reduced staining and favorable turbidity properties. The above-described components as well as optional components are described in detail below.

QUATERNARY AMMONIUM COMPOUND

Antibacterial antiplaque quaternary ammonium compounds include those in which one or two of the substituents on the quaternary nitrogen has a carbon chain length (typically alkyl group) of some 8 to 20, typically 10 to 18, carbon atoms while the remaining substituents (typically alkyl or benzyl group) have a lower number of carbon atoms, such as 1 to 7 carbon atoms, typically methyl or ethyl groups. Dodecyl trimethyl ammonium bromide, dodecyl dimethyl (2-phenoxyethyl) ammonium bromide, benzyl dimethylstearyl ammonium chloride, cetyl pyridinium chloride and quaternized 5-amino-1,3-bis(2-ethyl-hexyl)-5-methyl hexa hydropyrimidine are exemplary of typical quaternary ammonium antibacterial agents.

Another antibacterial antiplaque quaternary ammonium compound is benzethonium chloride, also known as Hyamine 1622 or diisobutylphenoxyethoxyethyl dimethyl benzyl ammonium chloride. In an oral preparation this material is highly effective in promoting oral hygiene by reducing formation of dental plaque, which is generally accompanied by a reduction in caries formation and periodontal diseases. Other cationic antibacterial agents of this type are those mentioned, for instance, in U.S. Pat. Nos. 2,984,639, 3,325,402, 3,431,208 and 3,703,583 and British Pat. No. 1,319,396.

The quaternary ammonium compound is used at a level of from about 0.02% to about 0.20%, preferably from about 0.025% to about 0.12%, in the present compositions.

The preferred compound for use in the present compositions is cetyl pyridinium chloride.

PYROPHOSPHATE SALT

The water soluble pyrophosphate salts useful in the present invention include tetra-alkali metal salts. These are commercially available materials. A more detailed description of the salts can be found in Kirk & Othmer, *Encyclopedia of Chemical Technology*, Second Edition, Volume 15, Interscience Publishers, Inc. (1968), pp. 232–276, incorporated herein by reference.

The preferred pyrophosphate salts useful herein are the tetrasodium and tetrapotassium salts, in both the hydrated as well as anhydrous states. The potassium salt is particularly preferred due to its greater solubility. The greater solubility provides for fewer formulating problems.

The pyrophosphate salts are used in the present compositons at a level sufficient to provide the $P_2O_7^{-4}$ species at a level of from about 0.5% to 5%, preferably from about 1% to 3%.

ACID

The acid useful in the compositions of the present invention can be any of a number of acids which are compatible with the quaternary ammonium active. Included are the mineral acids, sulfuric acid, nitric acid and hydrochloric acid as well as organic acids such as acetic and adipic acids. The preferred acid is sulfuric acid.

As indicated herein previously the amount of acid is an amount sufficient to adjust the pH to within the range of about 7.0 to 9.5, preferably from about 7.0 to 8.5.

CARRIER LIQUID

The carrier liquid in mouthwashes is generally a mixture of ethanol and water. Such mixtures often comprise about 60% to about 99% by weight of the composition, preferably from about 75% to 90%. The amount of ethanol is generally from about 5% to 60%, preferably about 5% to 25%. Water then constitutes the remainder of the carrier liquid mixture.

OPTIONAL COMPONENTS

The present mouthwashes generally contain other ingredients such as emulsifying agents, flavoring agents, sweeteners and humectants.

Suitable emulsifying agents for use in the present compositions include a variety of types with nonionic agents being preferred. The suitable nonionic emulsifying agents can be broadly defined as compounds produced by the condensation of alkylene oxide groups (hydrophilic in nature) with an organic hydrophobic compound which can be aliphatic, alkyl aromatic, or a condensate of an alkylene oxide with an alkylene glycol in nature. Examples of suitable nonionic emulsifying agents include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulphoxides, a mixtures of such materials.

The flavoring agents which can be added to the present compositions include such materials as oil of wintergreen, oil of peppermint, oil of spearmint, oil of sassafras, and physiological cooling agents such as those described in U.S. Pat. No. 4,230,688, Oct. 28, 1980 to Rowsell et al. Suitable sweetening agents include saccharin, dextrose, levulose, cyclamate, among many others. Suitable humectants include glycerine, sorbitol, xylitol and other agents which give a moist feel to the mouth.

Generally on a weight basis the mouthwashes of the present invention comprise from about 0% to 50%, preferably from about 5% to 20%, glycerine or other humectant, from about 0% to 2%, preferably from about 0.05% to 0.15%, emulsifying agent, from about 0% to 0.5%, preferably from about 0.025% to 0.5%, sweetening agent such as saccharin and from about 0% to 0.3%, preferably from about 0.05% to 0.3% flavoring agent.

METHOD OF MANUFACTURE

The compositions of the present invention are made using conventional mixing techniques. A typical method is described in Example I.

INDUSTRIAL APPLICABILITY

The present mouthwashes are used in a normal manner. The amount of mouthwash used is about 15 g and the time of residency in the mouth is about 15–30 seconds.

The following examples further describe and demonstrate the preferred embodiments within the scope of the present invention. Said examples are given solely for the purpose of illustration and are not to be construed as limitations of the present invention, as many variations are possible without departing from the spirit and scope thereof. Unless otherwise indicated, all percentages herein are by weight.

EXAMPLE I

The following is a composition representative of the present invention.

| Component | % |
| --- | --- |
| Cetylpyridinium chloride | 0.100 |
| Tetrapotassium Pyrophosphate (64.5% aqueous solution) | 8.820 |
| Ethanol (190 proof) | 5.500 |
| Sulfuric acid (10% aqueous solution) | 5.300 |
| Glycerine | 5.000 |
| Flavor | 0.070 |
| N,2,3-trimethyl-2-isopropyl butanamide | *0.050 |
| POE(20) Sorbitan Monoisostearate | 0.050 |
| Sodium Saccharin | 0.050 |
| Distilled Water | 75.060 |
| | 100.000 | pH = 7.5

*As taught in U.S. Pat. 4,230,688, October 28,1980 to Rowsell et al, incorporated herein by reference.

The above composition is formulated by making a first solution of the ethanol, surfactant, flavor and the butanamide material. The distilled water is then mixed with the pyrophosphate salt, saccharin and glycerine. To this water solution is added the first mixture and then in order sulfuric acid and cetylpyridinium chloride.

EXAMPLE II

The following is a composition representative of the present invention.

| Component | % |
| --- | --- |
| Cetylpyridinium chloride | 0.100 |
| Tetrapotassium Pyrophosphate (64.5% aqueous solution) | 8.820 |
| Ethanol (190 proof) | 5.500 |
| Acetic acid (10% aqueous solution) | 8.820 |
| Glycerine | 5.000 |
| Flavor | 0.070 |
| N,2,3-trimethyl-2-isopropyl butanamide | 0.050 |
| POE(20) Sorbitan Monoisostearate | 0.050 |
| Sodium Saccharin | 0.050 |
| Distilled Water | 71.540 |
| | 100.000 | pH = 7.5

EXAMPLE III

The following is a composition representative of the present invention.

| Component | % |
| --- | --- |
| Cetylpyridinium chloride | 0.100 |
| Tetrapotassium Pyrophosphate (64.5% aqueous solution) | 8.820 |
| Ethanol (190 proof) | 5.500 |
| Adipic acid | 0.940 |

-continued

| Component | % |
|---|---|
| Glycerine | 5.000 |
| Flavor | 0.070 |
| N,2,3-trimethyl-2-isopropyl butanamide | 0.050 |
| POE(20) Sorbitan Monoisostearate | 0.050 |
| Sodium Saccharin | 0.050 |
| Distilled Water | 79.420 |
| | 100.000 | pH = 7.5

What is claimed is:

1. A mouthwash composition comprising:
    (A) from about 0.02% to 0.20% of a quaternary ammonium compound;
    (B) an amount of a tetra-alkali metal pyrophosphate salt sufficient to provide from about 0.5% to 5% of the $P_2O_7^{-4}$ species; and
    (C) a carrier liquid
wherein the pH of said composition is adjusted to the range of from about 7.0 to 9.5 with a mineral or organic acid.

2. A mouthwash composition according to claim 1 wherein the amount of quaternary ammonium compound is from about 0.025% to 0.12%.

3. A mouthwash composition according to claim 2 wherein the carrier liquid is an ethanol/water mixture and is present at a level of from about 60% to 99%.

4. A mouthwash composition according to claim 3 wherein the pH of the composition is adjusted to the range of from about 7.0 to 8.5.

5. A mouthwash composition according to claim 4 wherein the acid is sulfuric acid.

6. A mouthwash composition according to claim 5 wherein the amount of the $P_2O_7^{-4}$ species is from about 1% to 3%.

7. A mouthwash composition according to claim 6 wherein the pyrophosphate salt is selected from the group consisting of tetrasodium pyrophosphate and tetrapotassium pyrophosphate.

8. A mouthwash composition according to claim 7 wherein the quaternary ammonium compound is cetyl pyridinium chloride.

9. A mouthwash composition according to claim 8 wherein the pyrophosphate salt is tetrapotassium pyrophosphate.

10. A mouthwash composition according to claim 9 which in addition contains an emulsifying agent, a humectant, a sweetener and a flavoring agent.

* * * * *